US 6,560,352 B2

(12) United States Patent
Rowe et al.

(10) Patent No.: US 6,560,352 B2
(45) Date of Patent: May 6, 2003

(54) APPARATUS AND METHOD OF BIOMETRIC IDENTIFICATION OR VERIFICATION OF INDIVIDUALS USING OPTICAL SPECTROSCOPY

(75) Inventors: Robert K. Rowe, Corrales, NM (US); Mark Ries Robinson, Albuquerque, NM (US); Steve L. Perella, Joliet, IL (US); Roxanne N. Landesman, Stanford, CA (US)

(73) Assignee: Lumidigm, Inc., Albuquerque, NM (US)

( * ) Notice: Subject to any disclaimer, the term of this patent is extended or adjusted under 35 U.S.C. 154(b) by 0 days.

(21) Appl. No.: 09/832,534

(22) Filed: Apr. 11, 2001

(65) Prior Publication Data

US 2002/0009213 A1 Jan. 24, 2002

Related U.S. Application Data

(63) Continuation-in-part of application No. 09/415,594, filed on Oct. 8, 1999.

(51) Int. Cl.⁷ .................................................. G06K 9/00
(52) U.S. Cl. .................... 382/115; 356/71; 340/5.52; 340/5.82; 250/339.02
(58) Field of Search ................................. 382/115, 124, 382/125, 126, 127; 73/73; 250/559.44, 316.1, 339.07, 339.1, 341.8; 340/5.52, 5.82; 356/31, 303, 445, 939, 71; 902/3; 707/6; 713/186; 702/19, 76

(56) References Cited

U.S. PATENT DOCUMENTS

RE29,008 E    10/1976    Ott .......................... 340/172.5

(List continued on next page.)

FOREIGN PATENT DOCUMENTS

EP    0 897 164 A2    2/1999    ............ G07C/9/00

(List continued on next page.)

OTHER PUBLICATIONS

U.S. patent application Ser. No. 09/415,600, Messerschmidt et al., filed Oct. 8, 1999.

(List continued on next page.)

*Primary Examiner*—Brian Werner
(74) *Attorney, Agent, or Firm*—Townsend and Townsend and Crew LLP

(57) ABSTRACT

Methods and apparatus for performing biometric identification or verification of identities using optical spectroscopy of tissue. Tissue optical spectra can be obtained by projecting optical radiation into skin and capturing the light transmitted or reflected back and out through the tissue. The tissue spectra collected preferably includes primarily light that has passed through skin tissue below the epidermis. Multiple tissue spectra and identities can be collected from one or more individuals. These tissue spectra can be analyzed on a computer, and the spectral features that are most important for classifying person-to-person differences can be established using principle component analysis, linear discriminant analysis, or a variety of other related techniques. One or more tissue spectra and identities can be collected from individuals for whom identification or verification may later be desired. A target individual seeking identification or verification can submit a suitable tissue site for spectroscopic measurement. In addition a target individual seeking identity verification can submit a purported identity using some means such as a typed user name, PIN code, magnetic card, transponder, etc. Similarity between the target spectrum and the spectrum or spectra in the enrolled spectral database with respect to the inter-person classification spectral features is determined and identification or verification is granted based on the degree of similarity.

45 Claims, 8 Drawing Sheets

U.S. PATENT DOCUMENTS

| | | | |
|---|---|---|---|
| 4,427,889 A | 1/1984 | Muller | 250/339 |
| 4,653,880 A | 3/1987 | Sting et al. | 350/620 |
| 4,655,225 A | 4/1987 | Dahne et al. | 128/633 |
| 4,661,706 A | 4/1987 | Messerschmidt et al. | 250/341 |
| 4,712,912 A | 12/1987 | Messerschmidt | 356/73 |
| 4,730,882 A | 3/1988 | Messerschmidt | 350/96.1 |
| 4,853,542 A | 8/1989 | Milosevic et al. | 250/353 |
| 4,859,064 A | 8/1989 | Messerschmidt et al. | 356/446 |
| 4,882,492 A | 11/1989 | Schlager | 250/346 |
| 4,944,021 A * | 7/1990 | Hoshino et al. | 382/5 |
| 4,975,581 A | 12/1990 | Robinson et al. | 250/339 |
| 5,015,100 A | 5/1991 | Doyle | 356/445 |
| 5,019,715 A | 5/1991 | Sting et al. | 250/571 |
| 5,028,787 A | 7/1991 | Rosenthal et al. | 250/341 |
| 5,051,602 A | 9/1991 | Sting et al. | 250/571 |
| 5,070,874 A | 12/1991 | Barnes et al. | 128/633 |
| 5,158,082 A | 10/1992 | Jones | 128/633 |
| 5,163,094 A * | 11/1992 | Prokoski et al. | 382/2 |
| 5,179,951 A | 1/1993 | Knudson | 128/633 |
| 5,222,496 A | 6/1993 | Clarke et al. | 128/633 |
| 5,225,678 A | 7/1993 | Messerschmidt | 250/339 |
| 5,311,021 A | 5/1994 | Messerschmidt | 250/339.01 |
| 5,321,265 A | 6/1994 | Block | 250/343 |
| 5,331,958 A | 7/1994 | Oppenheimer | 128/633 |
| 5,348,003 A | 9/1994 | Caro | 128/633 |
| 5,355,880 A | 10/1994 | Thomas et al. | 128/633 |
| 5,372,135 A | 12/1994 | Mendelson et al. | 128/633 |
| 5,379,764 A | 1/1995 | Barnes et al. | 128/633 |
| 5,402,778 A | 4/1995 | Chance | 128/633 |
| 5,435,309 A | 7/1995 | Thomas et al. | 128/633 |
| 5,452,723 A | 9/1995 | Wu et al. | 128/664 |
| 5,494,032 A | 2/1996 | Robinson et al. | |
| 5,533,509 A | 7/1996 | Koashi et al. | 128/633 |
| 5,559,504 A * | 9/1996 | Itsumi et al. | 340/825.3 |
| 5,636,633 A | 6/1997 | Messerschmidt et al. | 128/633 |
| 5,655,530 A | 8/1997 | Messerschmidt | 128/633 |
| 5,719,950 A | 2/1998 | Osten et al. | 382/115 |
| 5,761,330 A * | 6/1998 | Stoianov et al. | 382/127 |
| 5,792,050 A | 8/1998 | Alam et al. | 600/310 |
| 5,823,951 A | 10/1998 | Messerschmidt et al. | 600/322 |
| 5,830,132 A | 11/1998 | Robinson | 600/310 |
| 5,867,265 A | 2/1999 | Thomas | 356/328 |
| 5,935,062 A | 8/1999 | Messerschmidt et al. | |
| 5,999,637 A * | 12/1999 | Toyoda et al. | 382/124 |
| 6,069,689 A | 5/2000 | Zeng et al. | 356/73 |
| 6,122,042 A * | 9/2000 | Wunderman et al. | 356/73 |
| 6,154,658 A | 11/2000 | Caci | 455/466 |
| 6,317,507 B1 | 11/2001 | Dolfing | 382/119 |
| 6,330,346 B1 * | 12/2001 | Peterson et al. | 382/115 |

FOREIGN PATENT DOCUMENTS

| | | | |
|---|---|---|---|
| EP | 0 924 656 A2 | 6/1999 | G07C/9/00 |
| WO | WO 92/17765 | 10/1992 | G01N/21/31 |
| WO | WO 93/07801 | 4/1993 | A61B/5/00 |
| WO | WO 01/18332 A1 | 3/2001 | E05B/49/00 |
| WO | WO 01/27882 A2 | 4/2001 | |

OTHER PUBLICATIONS

Bantle, John P. et al., "Glucose Measurement in Patients with Diabetes Mellitus with Dermal Interstitial Fluid," Copyright © 1997 by Mosby–Year Book, Inc., 9 pages.

Marbach, Ralf, "Noninvasive blood Glucose Assay by Near–Infrared Diffuse Reflectance Spectroscopy of the Human Inner Lip," *Applied Spectroscopy*, vol. 47, No. 7 (1993) pp. 875–881.

Mardia, K. V. et al., *Multivariate Analysis*, Academic Press (1979) pp. 300–325.

Ripley, B.D. *Pattern Recognition and Neural Networks*, Cambridge University Press (1996) pp. 91–120.

Service, F. John et al., "Spectal Interstitial Glucose as an Indicator of Ambient Glycemia," *Diabetes Care*, vol. 20, No. 9, Sep. 1997, 9 pages.

Webb, Paul, "Temperatures of Skin, Subcutaneous Tissue, Muscle and Core in Resting Men in Cold, Comfortable and not Conditions," *European Journal Applied Physiology*, vol. 64 (1992) pp. 471–476.

* cited by examiner

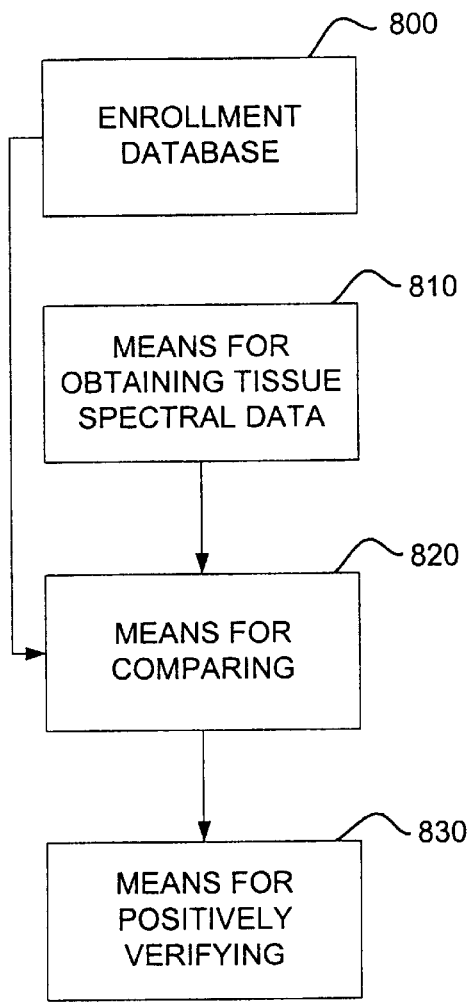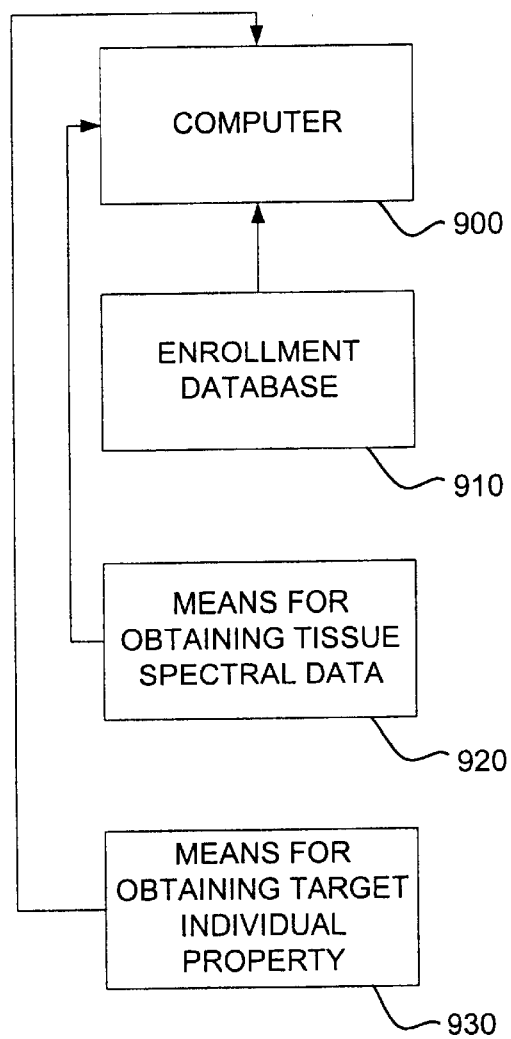
Fig. 8
Fig. 9

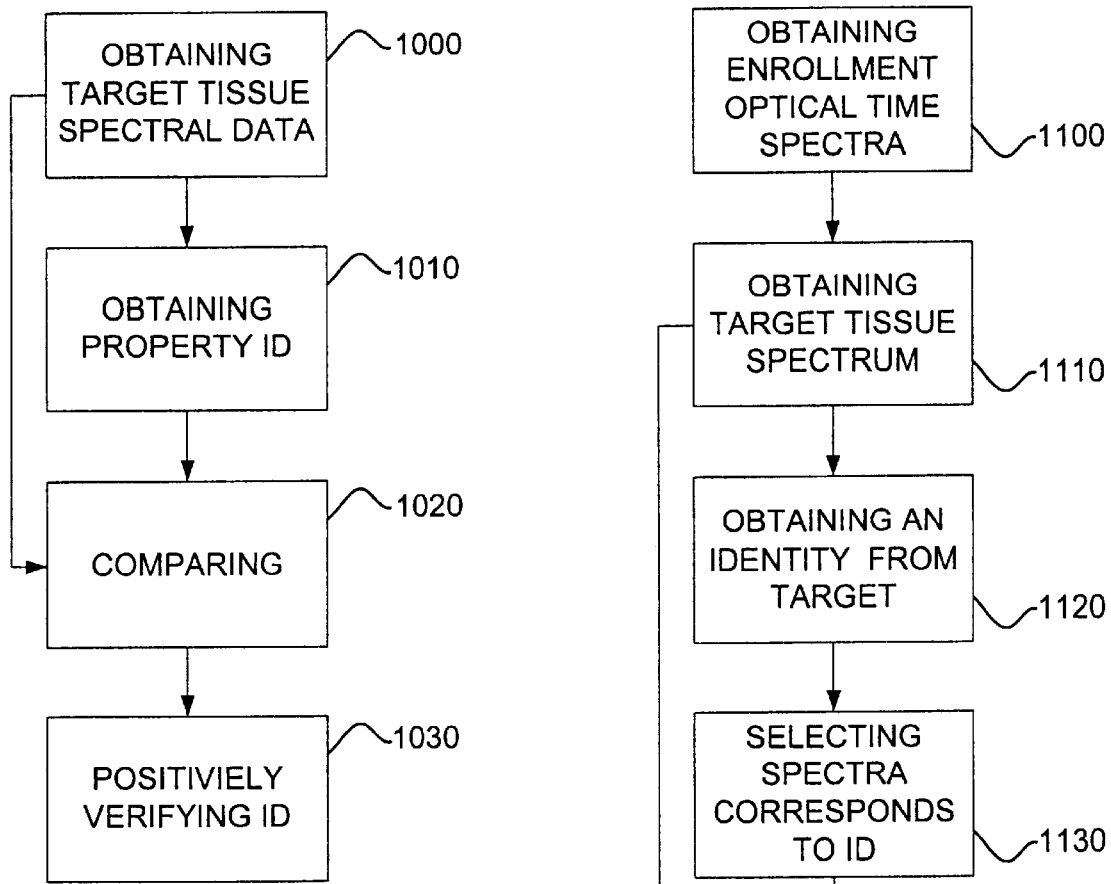
Fig. 10
Fig. 11
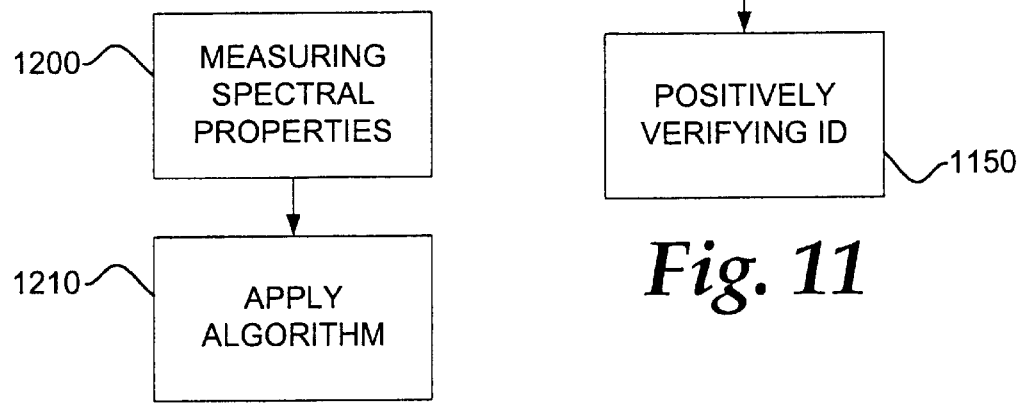
Fig. 12

APPARATUS AND METHOD OF BIOMETRIC IDENTIFICATION OR VERIFICATION OF INDIVIDUALS USING OPTICAL SPECTROSCOPY

CROSS REFERENCE TO RELATED PATENTS AND PENDING APPLICATIONS

The present application is a continuation-in-part of U.S. patent application Ser. No. 09/415,594, filed Oct. 8, 1999, entitled "Apparatus and Method for Identification of Individuals by Near-Infrared Spectrum"; which is related to U.S. patent application Ser. No. 09/174,812, filed Oct. 19, 1998, entitled "Method for Non-Invasive Analyte Measurement with Improved Optical Interface", now U.S. Pat. No. 6,152,876; and U.S. patent application Ser. No. 08/871,366, filed Jun. 9, 1997, entitled "Diffuse Reflectance Monitoring Apparatus", now U.S. Pat. No. 5,935,062, all assigned to the same assignee as the present application, and the disclosures of which are incorporated herein by reference.

TECHNICAL FIELD

The present invention relates generally to methods and systems for performing biometric identification of unknown individuals or verifying the identity of an individual utilizing optical spectral data from tissue. More specifically, the invention relates to methods and apparatus for biometric identification or verification of a living individual using optical energy in the near-ultraviolet, visible or near-infrared regions or combinations of wavelengths from these regions to measure the absorption and scattering of the light energy by tissue below the epidermis. The spectral features imposed by tissue on an incident optical radiation are unique to an individual and suitable for biometric determinations. Such determinations are made by using multivariate classification techniques to compare current tissue spectra with previously stored tissue spectral data contained in an enrollment database.

BACKGROUND OF THE INVENTION

Biometric identification describes the process of using one or more physical or behavioral features to identify a person or other biological entity. There are two common modes in which biometric identification occurs: one-to-many (identification) and one-to-one (verification). One-to-many identification attempts to answer the question of, "do I know you?" The biometric measurement device collects a set of biometric data from a target individual. From this information alone it assesses whether the person was previously enrolled in the biometric system. Systems that perform the one-to-many identification task such as the FBI's Automatic Fingerprint Identification System (AFIS) are generally very expensive (several million dollars or more) and require many minutes to detect a match between an unknown sample and a large database containing hundreds of thousands or millions of entries. The one-to-one mode of biometrics answers the question of, "are you who you say you are?" This mode is used in cases where an individual makes a claim of identity using a code, magnetic card, or other means, and the device uses the biometric data to confirm the identity of the person by comparing the target biometric data with the enrolled data that corresponds with the purported identity.

There also exists at least one variant between these two modes. This variant occurs in the case where a small number of individuals are contained in the enrolled database and the biometric application requires the determination of only whether a target individual is among the enrolled set. In this case, the exact identity of the individual is not required and thus the task is somewhat different (and often easier) than the identification task described above. This variant might be useful in applications where the biometric system is used to secure an expensive, dangerous, or complex piece of machinery. In this example, only authorized people should be able to use the equipment, but it might not be of interest to determine specifically which of the authorized personnel are using it at a particular time.

Although in general the one-to-many identification task is more difficult than one-to-one, the two tasks become the same as the number of recognized or authorized users for a given biometric device decreases to just a single individual. Situations in which a biometric identification task has only a small number of entries in the authorization database are quite common. For example, biometric access to a residence, to a personal automobile, to a personal computer, to a cellular telephone, to a handgun, and other such personal devices typically require an authorization database of just a few people.

Biometric identification and verification are useful in many applications. Examples include verifying identity prior to activating machinery or gaining entry to a secure area. Another example would be identification for matching an individual to records on file for that individual, such as for matching hospital patient records when the individual's identity is unknown. Biometric identification is also useful to match police records at the time a suspect is apprehended, but true identity of the suspect is not known. Additional uses of biometric identification or verification include automotive keyless start and entry applications, secure computer and network access, automated financial transactions, authorized handgun use, and time-and-attendance applications.

Current methods for biometric identification are manifold, but some of the most common techniques include fingerprint pattern matching, facial recognition, hand geometry, iris scanning, and voice recognition. Each of these technologies addresses the need for biometric identification to some extent. However, due to cost, performance, or other issues, each of the existing methods has advantages and disadvantages relative to the other technologies.

One present biometric product on the market is known as the LiveGrip™, made by Advanced Biometrics, Inc. This product is based on the technology disclosed in U.S. Pat. No. 5,793,881, by Stiver et al. In this patent, Stiver et al. disclose an identification system that is a security device, which consists of a cylindrical or elongated transparent shell with an internal light source and a means to scan the hand of the person grasping the shell to record the internal structure or subcutaneous structure of the hand using an imaging methodology. The system uses near-infrared light to image the pattern of blood vessels and associated tissue in the hand. The LiveGrip™ product based on this patent is claimed to have reduced the ability for an intruder to fool the biometric system, as they claim can be easily done using a latex mold with many finger print readers or hand-geometry systems. However, the imaging approach requires good quality optics and/or detector arrays that add to both system complexity and cost. Further, the system relies on imaging blood vessels, and therefore, requires that the same site be presented to the system in use as during enrollment and further requires that the repositioning of the site is accurate enough to allow the software to align the two images to confirm identity. Finally, the size of the sensor head is limited to the portion of the hand that must be imaged for accurate identification.

Living human tissue is recognized as a dynamic system containing a multitude of components and analyte information that is particularly useful in the medical profession for diagnosing, treating and monitoring human physical conditions. To this end, effort has been directed toward developing methods for non-invasive measurement of tissue constituents using spectroscopy. The spectrographic analysis of living tissue has been focused on the identification of spectral information that defines individual analytes and relates such spectral data to the analyte's concentration. Concentrations of these analytes vary with time in an individual person. Acquiring tissue spectral data with sufficient accuracy for use in diagnosis and treatment has proven difficult. Difficulties in conducting the analysis have been found that are related to the fact that the tissue system is a complex matrix of materials with differing refractive indices and absorption properties. Further, because the constituents of interest are many times present at very low concentrations, high concentration constituents, such as water, have had a detrimental impact on identifying the low level constituent spectral information and giving an accurate reading of the desired constituent concentration. Development of these techniques has always focused on the changes in spectral output with change in concentration of a dynamic analyte of interest, such as glucose. The techniques disclosed are focused on identifying concentrations of specific analytes, the concentration of which is expected to vary with time.

Improved methods and apparatus for gathering and analyzing a near-infrared tissue spectrum for an analyte concentration are disclosed in commonly assigned U.S. patent applications and issued patents. U.S. Pat. No. 5,655,530 and U.S. Pat. No. 5,823,951, filed Apr. 18, 1997, entitled "Method for Non-invasive Blood Analyte Measurement with Improved Optical Interface" relate to near-infrared analysis of a tissue analyte concentration that varies with time, with a primary focus on glucose concentrations in diabetic individuals. The methods and apparatus include placing a refractive index-matching medium between a sensor and the skin to improve the accuracy and repeatability of testing. U.S. patent application Ser. No. 09/174,812, filed Oct. 19, 1998, entitled "Method for Non-Invasive Blood Analyte Measurement with Improved Optical Interface," now U.S. Pat. No. 6,152,876, discloses additional improvements in non-invasive living tissue analyte analysis. The disclosure of each of these three applications or patents are hereby incorporated by reference.

U.S. Pat. No. 5,636,633 relates, in part, to another aspect of accurate non-invasive measurement of an analyte concentration. The apparatus includes a device having transparent and reflective quadrants for separating diffuse reflected light from specular reflected light. Incident light projected into the skin results in specular and diffuse reflected light coming back from the skin. Specular reflected light has little or no useful information and is preferably removed prior to collection. U.S. Pat. No. 5,935,062, filed Jun. 9, 1997, entitled "Improved Diffuse Reflectance Monitoring Apparatus", discloses a further improvement for accurate analyte concentration analysis which includes a blocking blade device for separating diffuse reflected light from specular reflected light. The blade allows light from the deeper, inner dermis layer to be captured, rejecting light from the surface, epidermis layer, where the epidermis layer has much less analyte information than the inner dermis layer, and contributes noise. The blade traps specular reflections as well as diffuse reflections from the epidermis. The disclosures of the above patent and application, which are assigned to the assignee of the present application, are also incorporated herein by reference.

U.S. Pat. No. 5,435,309 relates to a system for selecting optimal wavelengths for multivariate spectral analysis. The use of only one wavelength gives insufficient information, especially for solutions having multiple components. The use of too many wavelengths can include too much noise and lead to combinatorial explosion in calculations. Therefore, the number of wavelengths used should be limited and the wavelengths well chosen. Genetic algorithms are used in this reference to select the most fit wavelengths. The disclosure of this patent is incorporated herein by reference.

SUMMARY OF THE INVENTION

The present invention includes methods and apparatus for biometric identification or verification of individuals using optical spectroscopy in the near ultraviolet, visible or near-infrared spectral regions and combinations of those spectral regions. The methods and apparatus disclosed provide superior performance relative to current biometric systems as well as provide other advantages. Prior art biometric identification devices have the distinct disadvantage of requiring the use of specific body parts in order to achieve their techniques. For example, fingerprint devices require that only the extreme ventral portion of the fingers can be used as the biometric site. The methods and apparatus of the present invention enable biometric identification to occur with finger, palms, wrists, forearms and other convenient sites on the body. Further, even in the case of using fingers, the present invention allows use of multiple sites along the finger on both the dorsal or ventral surfaces. Present finger print readers require that the same finger be presented to the reader for identification or verification that was presented during the enrollment analysis. The present invention can use different fingers (or other sites) for enrollment and for subsequent verification. This capability provides for increased enrollment efficiency since the user only has to present one enrollment site to the system, but also provides critical flexibility during the use of the device. An example of this flexibility is the case where the user has enrolled a site on a particular hand and that particular site is unavailable for subsequent analysis due to some injury or some severe surface contamination of the site. This spectroscopic-based biometric system of the present invention can operate on the site from the other hand without previous enrollment of such site. Further, although the results below are based on optical systems that require contact with the skin surface, the optical system such as that disclosed in U.S. Pat. No. 5,636,633 or U.S. Pat. No. 5,935,062 discussed previously could be used in the present invention to generate similar data in a non-contact mode. Such a non-contact biometric sensor apparatus would have significant advantages when installed in public locations to minimize wear and contamination issues associated with critical optical elements.

The present invention is based on applicant's recognition that the resultant tissue spectrum of a particular individual includes unique spectral features and combinations of spectral features that can be used to identify the individual once the analytical device has been trained to identify the individual. The apparatus of the present invention performs biometric analysis using near-ultraviolet, visible, very near-infrared, or near-infrared energy and combinations thereof. In particular, the applicants have been able to demonstrate that the near infrared spectral data in the range from 1.25–2.5 $\mu$m as collected with a near-infrared spectroscopic system can be used for spectral biometric determinations of identity or verification of identity. As well, the applicants have also shown that near-ultraviolet, visible and very near-infrared spectral data in the range from 350–1000 nm can also be used to perform biometric determinations. Although either or both of the aforementioned spectral regions can be used, the latter region may be advantageous due to the lower cost and generally higher performance of the silicon detectors that can be incorporated in systems operating in this spectral region.

In order to use the present invention for biometric tasks, the device and the algorithms need to be constructed to optimize performance in this application. Applicants have been able to achieve high accuracy rates with the techniques disclosed herein, even though the tissue being analyzed is a dynamic system with analyte concentrations, and thus, tissue spectral data, varying considerably over time and between analysis. Success of the method of the present invention is believed tied to at least two components.

First, the method incorporates an apparatus and technique for accurately and repeatably acquiring a tissue spectrum that minimizes effects due to instrumental, environmental and sampling changes, while remaining sensitive to slight changes in the spectral properties of tissue at any given wavelength. The system optimizes optical throughput both into and out of the tissue sample. Second, because the spectral features or combinations of spectral features that are unique for a particular individual are not readily apparent or identified by visual comparison of a spectral result, the present invention relies on discriminant analysis techniques to first train the device to identify spectral features of significance for the individual and then compare such features to new spectral data at the time of attempted identification or verification. The present invention incorporates discriminant analysis methods such as those based upon Mahalanobis distances, spectral residual magnitudes, K-nearest-neighbor methods, or linear or nonlinear discriminant techniques to compare spectral data acquired from an individual with spectral data present in a database.

The present invention, thus, includes a method for identifying or verifying the identity of an individual using non-invasive tissue spectroscopy. Depending on the tissue site and the wavelength range, the spectral data may be collected in a transmission or reflectance configuration. A preferred method and apparatus illuminates skin with selected radiation and collects the reflected, non-absorbed selected radiation. Diffuse, rather than specular, reflected light is preferably collected, more preferably light diffusely reflected from the dermis and deeper tissue rather than the epidermis. The spectral data collected can be stored in a computer database.

There are three major data elements associated with the present invention: calibration, enrollment and target spectral data. The calibration data are used to establish spectral features that are important for biometric determinations. This set of spectral data consists of series of tissue optical spectral data that are collected from an individual or individuals of known identity. Preferably, these data are collected over a period of time and a set of conditions such that multiple spectra are collected on each individual while they span nearly the full range of physiological states that a person is expected to go through. As well, the instrument or instruments used for spectral collection should also span the full range of instrumental and environmental effects that it or sister instruments are likely to see in actual use. These calibration data are then analyzed in such a way as to establish spectral wavelengths or "factors" (i.e. linear combinations of wavelengths or spectral shapes) that are sensitive to between-person spectral differences while being insensitive to within-person effects as well as instrumental effects (both within- and between-instruments) and environmental effects. These wavelengths or factors are then used subsequently to perform the biometric determination tasks.

The second major set of spectral data used for biometric determinations are the authorized or enrollment spectral data. Enrollment spectra are collected from individuals who are authorized or otherwise required to be recognized by the biometric system. Enrollment spectra can be collected over a period of seconds or minutes. Two or more optical samples can be collected from the individual to ensure similarity between the samples and rule out a sample artifact in one of the samples. If such an artifact is found, additional enrollment spectra can be collected. These spectral data can either be averaged together or otherwise combined, or stored separately. In either case, the data are stored in an enrollment database. In most cases each set of enrollment data are linked with an identifier for the persons on whom the spectra were measured. In the case of an identification task, the identifier can be used for record keeping purposes of who accessed the biometric system at which times. For a verification task, the identifier is used to extract the proper set of enrollment data against which verification is performed.

The third and final major set of data used for the spectral biometric system is the spectral data collected when a person attempts to use the biometric system to identify them or verify their identity. These data are referred to as target spectra. They are compared to the appropriate enrollment spectrum or spectra using the classification wavelengths or factors determined from the calibration set to determine the degree of similarity. If the target and enrollment spectra are sufficiently similar, the biometric determination is made. If the similarity is inadequate, then the biometric determination is cancelled and a new target measurement may be attempted. In the case of identification, the system compares the target spectrum to all of the enrollment spectra and reports a match if one or more of the enrolled individual's data is sufficiently similar to the target spectrum. If more than one enrolled individual matches the target, then either all of the matching individuals can be reported, or the best match can be reported as the identified person. In the case of verification, the target spectrum is accompanied by a purported identity that is collected using a magnetic card, a typed user name, a transponder, a signal from another biometric system, or other means. This identifier is then used to retrieve the corresponding set of spectral data from the enrollment database, against which the biometric similarity is made and the identity verified or denied.

In one method of verification, principle component analysis is applied to the calibration data to generate spectral factors. These factors are then applied to the spectral difference taken between a target spectrum and an enrollment spectrum to generate Mahalanobis distance and spectral residual magnitude values as similarity metrics. Identify is verified only if the aforementioned distance and magnitude are less than a predetermined threshold set for each. Similarly, in a preferred method for biometric identification, the Mahalanobis distance and spectral residual magnitude are calculated for the target spectrum relative to each of the database spectra. Identify is established as the person or persons associated with the database spectra that gave the smallest Mahalanobis distance and spectral residual magnitude that is less than a predetermined threshold set for each.

One system for performing biometric tasks includes: a computer having an input device and an output device; a database including selected tissue spectral data for enrolled persons; a radiation or light source for projecting selected radiation into sub-epidermal tissue; a sampler to interface with tissue; a spectrometer including a detector for measuring subcutaneous radiation intensity over a plurality of wavelengths; and a classification program running in the computer for assessing the degree of similarity between a plurality of optical spectra by applying a set of classification factors. The program can include software for performing discriminant analysis. As well, the program can include a separate module to collect additional authorized spectral data or to remove existing spectral data from the database. In the case of using the spectral biometric system for verification tasks, the system will also include some means of establishing the purported identity of the person attempting to gain access. Methods to collect the purported identity include, but are not limited to, magnetic cards, PIN code, keyboard entry of the name or ID, voice command, transponder, etc.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views:

FIG. 8 is a block diagram depicting a preferred spectroscopic system method;

FIG. 9 is a block diagram showing an alternate method of a spectroscopic system;

FIG. 10 is a block diagram describing a spectroscopic system process;

FIG. 11 is a block diagram showing an alternate process for a spectroscopic system; and FIG. 12 depicts the components of a process using a preferred spectroscopic system.

DETAILED DESCRIPTION OF THE PREFERRED EMBODIMENTS

Figure 1:
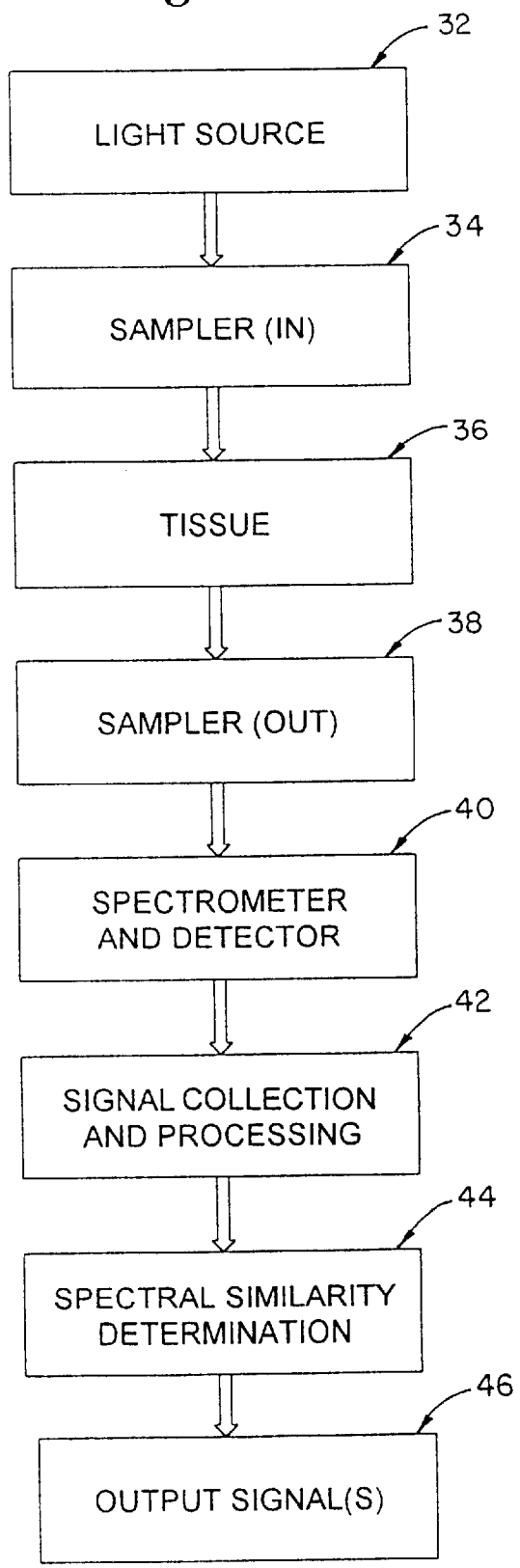
FIG. 1 is a block diagram of components incorporated into a preferred biometric analyzer.

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

The present invention is based on Applicant's recognition that an accurate, precise and repeatable tissue spectra of an individual in the near ultraviolet range, visible range, very near infrared, near infrared range and combinations of these ranges contains spectral features and combinations of spectral features which are unique to that individual. Throughout this disclosure, spectral data spanning the near-ultraviolet, visible and very near-infrared regions from 350 nm to 1000 nm will be referred to as silicon-region data due to the fact that this is substantially the spectral region over which silicon detectors are sensitive.

The present invention is further based on a recognition that proper analysis, utilizing discriminant analysis techniques, can identify these unique features or combinations, which are not readily apparent in visual analysis of a spectral output, so that an individual's identity may be verified by comparison of tissue spectral data taken at the time of verification compared to stored tissue spectral data from prior testing. The identification methods can also be used in conjunction, or simultaneously, with measurement of analyte concentrations in an individual. As well, the biometric methods of the present invention can be used in conjunction with other biometric techniques to either increase the accuracy of the system, or offer more than one method to identify a person in case one method is disabled due to system failure or other reason.

Prior spectral data is used to train the device to identify a particular person based on features that are recognized unique to that particular individual. These unique spectral features have been found to be consistently present even though the tissue being analyzed at each time of analysis is a dynamic system which contains components and analytes whose concentration vary, with resulting tissue spectral variations, due to physiological changes in the individual.

As previously stated and shown in FIG. 12, there are two components believed of importance to the success of the method of the present invention. First, the method incorporates an apparatus and technique for accurately and repeatably acquiring a tissue spectrum 1200 that minimizes effects due to instrumental, environmental and sampling changes, while remaining sensitive to slight changes in the spectral properties of tissue at any given wave length. As well, the system optimizes optical throughput both into and out of the tissue sample. Second, the method requires specific techniques, such as an algorithm 1210, for training the instrument to identify spectral features of significance for that particular individual, and then to compare such features to new spectral data acquired at the time of attempted verification or identification. Because the spectral features or combinations of spectral features that are unique for a particular individual are not readily apparent or identified by visual comparison of a spectral result and the unique spectral features are present at different wavelengths for different individuals, the present invention relies on discriminant analysis techniques to compare spectral data. Each component of the apparatus and method of the present invention are detailed below.

Referring now to FIG. 1, a block diagram of a preferred overall spectroscopic system of the present invention is shown. The system generally includes a light source 32 that provides light energy at selected wavelengths to the input side of an optical sampler 34. The light passes from the input of the sampler 34 into the tissue 36. Once in the tissue 36, a portion of the light passes into the output side of the sampler 38, which then enters a spectrometer 40. The signal collected by the detector in the spectrometer 40 is digitized and sent to a processing subsystem 42 with the data analyzed within a spectral similarity determination subsystem 44, which in turn provides the proper output 46 based on the data. The output may simply be a yes or no determination of whether a person is who they allege to be or, alternatively, the system may output an identification of an unknown individual.

In acquiring tissue spectral data, measurements can be made in at least two different modes. It is recognized that one can measure light transmitted through a section of tissue, or one may measure light reflected from tissue. Although light in such regions as the silicon-region can penetrate tissue to significant depths of one centimeter or more, depending upon the wavelength, transmission sampling of the tissue limits the region of the body that can be used. Thus, while either mode of sampling is applicable to the present invention, and especially to analysis utilizing light in the silicon-region, a preferred and more versatile sampling method is based upon reflected light.

Photons reflect and refract at refractive index discontinuities, and so light impinging on tissue immediately has a small reflectance at the tissue surface. This is referred to as specular reflectance. Since this light does not penetrate into the tissue, it contains little information about the tissue constituents. This is especially true in light of the physiology of skin, which possesses an outward layer which is essentially dead and lacks spectral information believed unique to an individual. Thus, reflected light energy containing spectral data unique to an individual is believed to be that light which is reflected back to the surface through refractive index discontinuities deeper within the tissue sample. This reflected light energy is referred to as diffusely reflected light.

Applicants have found that a large fraction of incident photons are absorbed and scattered in the tissue. Those photons which are available for coupling back out of the tissue are likely diverted in their angular path. In fact, by definition, a photon must change direction in order to exit the tissue in a direction towards the input optic when light is collected using a diffuse reflectance sampler. Applicants, however, have found that one problem with detection is associated with the refractive index discontinuity between the average tissue refractive index and the refractive index of air outside of the tissue. It has been found that this discontinuity acting on incident light leads to a refraction and a small specular reflectance of less than about 5 percent. However, on the way out, the discontinuity gives rise to a critical angle phenomenon. Because the photon is traveling from a high refractive index medium to a lower one, a critical angle exists above which a photon is totally internally reflected and will not escape the tissue sample. This critical angle for photons traveling from tissue to air has been found to be about 46 degrees, which presents a problem. A photon normally incident on the tissue surface must deviate through a large angle to exit. Because of the forward directionality of scattering, this is difficult for a photon to do, and it is very likely to make a grazing or high angle incidence with the tissue and air interface. The grazing incidence photons will not escape because the critical angle is exceeded. Embodiments of the present invention include features to overcome this problem and assure that additional, high-incidence-angle light can be received by the output of the optical sampler 38.

The use of a blocker blade device or functionally similar spacing of input and output light alleviates much of the problem created by changes in the refractive index, reducing the resulting specular reflections. Loss of light due to the critical angle problem at the tissue-air interface results in a slight decrease in the measurement signal-to-noise ratio, which may be tolerable for many biometric determination applications.

An alternative solution for the differences in refractive index associated with coupling light energy exiting tissue to an analytical instrument is the use of an immersion fluid which has very low absorptivity in the spectral range of interest, and has a viscosity compatible with good flow and coverage, while having a refractive index which effectively introduces light into the tissues, reduces specular reflection and effectively gets light back out of the tissue.

Figure 2:
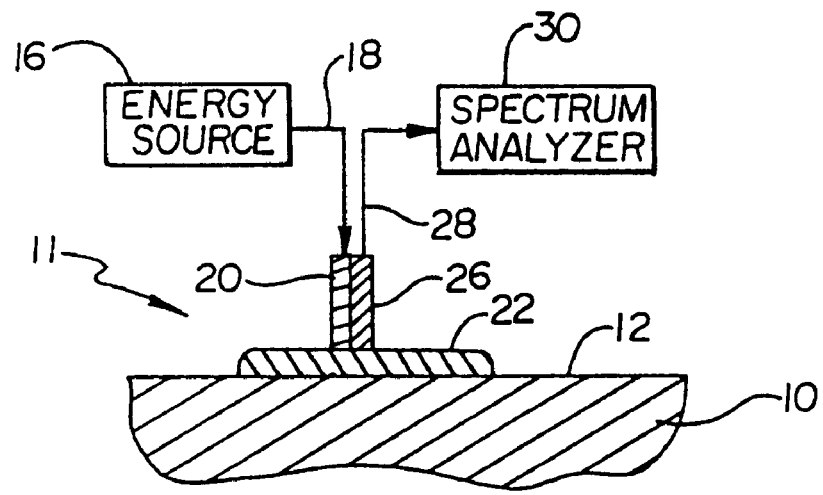
FIG. 2 is a partial cross-sectional view of a sensor element coupled to the skin surface via an indexing-matching fluid.
Figure 3:
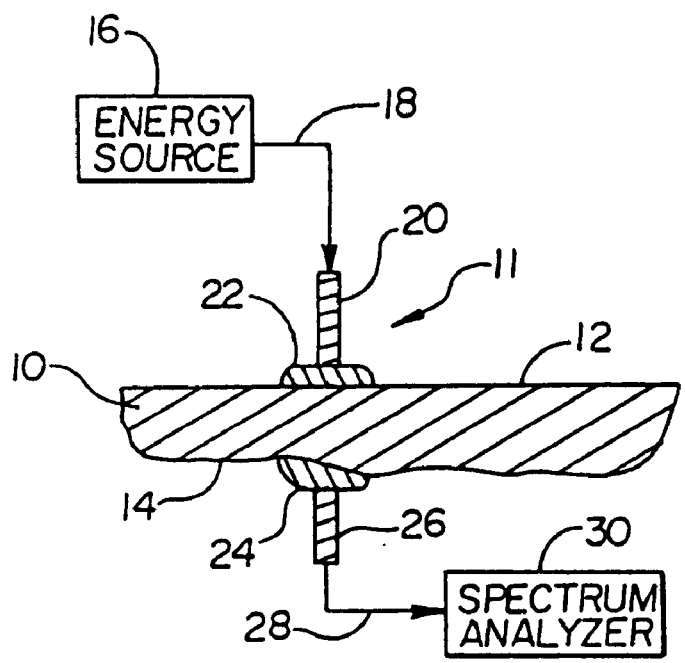
FIG. 3 is a partial cross-sectional view of an alternative embodiment of a sensor element coupled to opposite sides of a skin surface via an indexing-matching fluid.

Now referring to FIGS. 2 and 3, partial cross-sectional views of two preferred embodiments of an apparatus for non-invasively acquiring a tissue spectrum are depicted. The depictions in FIGS. 2 and 3 are schematic to depict the concept of utilizing a non-invasive sensor element 11 operatively connected to an energy source 16 and a spectrum analyzer 30. The relative size, shape and detail of physical components are not depicted. Each Figure also depicts use of an optional index-matching medium 22.

The apparatus depicted in FIG. 2 and the apparatus depicted in FIG. 3 generally include three elements, an energy source 16, an optical sensor element 11, and a spectrum analyzer 30. The embodiment of FIG. 2 depicts the sensor element 11 as including an input element 20 and an output element 26, which can include a single lens system for both input and output light energy. The input element 20 and output element 26 are in contact with a common skin surface 12 of the selected tissue 10. The alternative embodiment of FIG. 3 depicts an alternative sensor element 11 arrangement, wherein the input element 20 and output element 26 are arranged on opposing surfaces 12, 14 of tissue 10. Both embodiments function to give a measure of the absorption of light energy by the tissue 10. However, the embodiment of FIG. 2 is utilized to measure the quantity of light energy that is diffusely reflected from the tissue 10 by the components or features therein. In contrast, the embodiment of FIG. 3 measures the transmission of light energy through the tissue 10. In either embodiment, the absorption at various wavelengths can be determined by comparison to the intensity of the light energy from the energy source 16.

The energy or light source 16 can be selected from many available designs. In one embodiment, a wide band, infrared black body source is utilized with preferred optical wavelengths emitted from the energy source 16 between 1.0 and 2.5 $\mu$m. Light source 16 can also preferably be a light source emitting light in the silicon-region of the spectrum, which is defined as the spectral range over a silicon detector is active and is roughly between 350 and 1000 nm. Light sources can be based upon quartz tungsten halogen incandescent bulbs, broad-band light emitting diodes (LEDs), collections of laser diodes or vertical cavity surface emitting lasers (VCSELS), globe bars, or a variety of other optical sources known in the art. The light energy must be relayed to the tissue and the sampler 36 of appropriate design can be utilized. The device can consist of optical fibers to deliver the light to the proper location on the tissue. This type of design is shown schematically in FIGS. 2 and 3. The energy source 16 is operatively coupled to a first means for transmitting infrared energy 18 from the energy source to the input element 20. In preferred embodiments, this first means 18 is simply the transmission of light energy to the input element 20 through air by placing the energy source 16 proximate the input element 20.

The input element 20 of the sensor element 11 can include optical fibers or an optical lens which focuses the light energy to a high energy density spot. However, it is understood that other beam focusing means may be utilized in conjunction with the optical lens to alter the area of illumination. For example, a multiple lens system, tapered fibers, or other conventional optical beam-shaping devices could be utilized to alter the input light energy. In other preferred embodiments, the sampler 36 can be of a non-fiber design consisting of a compound parabolic concentrated (CPC) to concentrate the light at the sample site, as disclosed in the above cited U.S. patent Application entitled "Encoded Variable Filter Spectrometer."

Once the light interacts with the tissue, it can be collected in a manner similar to the illumination methods. An appropriate arrangement of optical fibers can be used, or a non-fiber collection device such as a CPC may be employed.

In both embodiments depicted in FIGS. 2 and 3, an output sensor 26 is utilized to receive reflected or transmitted light energy from the tissue 10. In a preferred embodiment, a specular control device is incorporated to separate the specular reflected light from diffusely reflected light. Such devices are disclosed in co-pending and commonly assigned U.S. Pat. No. 5,935,062, filed Jun. 9, 1997, and entitled "Diffuse Reflectance Monitoring Apparatus", the disclosure of which is incorporated herein by reference. As described in conjunction with a method of analysis below, the embodiment of FIG. 2 has an output sensor 26 which receives reflected light energy, while the embodiment of FIG. 3 includes an output sensor 26 which receives transmitted light through the tissue 10. As with the input element 20, the output element 26 is preferably an optical lens. Other optical collection means may be incorporated into an output element 26, such as a multiple lens system, tapered fiber, or other beam-collection means to assist in directing the light energy to the spectrum analyzer 30.

A second means for transmitting infrared energy 28 is operatively connected to the output element 26. The light transmitted through the second means for transmitting infrared energy 28 is transmitted to the spectrum analyzer 30. In a preferred embodiment, the operative connection to the output element includes transmission of the reflected or transmitted light energy exiting the output element through air to the spectrum analyzer 30. A mirror or series of mirrors may be utilized to direct this light energy to the spectrum analyzer.

In practicing the method of the present invention, tissue 10 area is selected as the point of analysis. This area can include the skin surface 12 on the dorsal or ventral surfaces of the fingers and thumbs, dorsal or ventral surfaces of the wrist, the web between the thumb and index finger, the thenar eminence, the hypothenar eminence, the medical medial hypothenar eminence, the earlobe, the temple, forearm, or any other skin surface. Preferably, the area for sampling is a relatively smooth, uncalloused surface. Optionally, a quantity of an index-matching medium 22, whether fluid or deformable solid, can be placed on the skin surface 12 in the area to be analyzed to couple the sensor element 11, which includes the input element 20 and the output element 26 to the instrument.

In acquiring spectral data of the tissue 10, light energy from the energy source 16 is transmitted through the first means for transmitting infrared energy 18 into the input element 20. The light energy is transmitted from the input element 20 through the index-matching medium 22, to the skin surface 12. The light energy contacting the skin surface 12 is differentially absorbed by the various components and analytes contained below the skin surface 12. In a preferred embodiment, the non-absorbed light energy is reflected back to the output element 26 upon propagating again through the optional index-matching medium 22. The non-absorbed light energy is transmitted via the second means for transmitting infrared energy 28 to the spectrum analyzer 30.

In the alternative embodiment of FIG. 3, the light energy propagated through the input element 20 and first quantity of index-matching medium 22 is differentially absorbed by the tissue 10, while a quantity of the light energy at various wavelengths is transmitted through the tissue 10 to the opposing or second skin surface 14. From the second skin surface 14, the non-absorbed light energy is propagated through the second quantity of optional index-matching medium 24 to the output element 26 with subsequent propagation to the spectrum analyzer 30 for producing the tissue spectrum. Tissue sites that can be used for transmission sampling can include fingers and thumbs, the web between the thumb and index finger, the earlobe, or any other skin surface surrounding a relatively thin portion of the anatomy. Preferably, the area for sampling is a relatively smooth, uncalloused surface.

In FIG. 1, the spectrometer subsystem 40 can include a variety of methods and apparatus. A preferred method of detecting optical spectra is achieved based upon optical interference phenomena such as in a Fourier transform infrared spectrometer system. One such system is disclosed in commonly assigned U.S. patent application Ser. No. 09/832,585, entitled "System for Non-Invasive Measurement of Glucose in Humans," filed on even date herewith, and U.S. patent application Ser. No. 09/832,631, entitled "Encoded Variable Filter Spectrometer," filed on even date herewith, the disclosures of which are both incorporated herein by reference. Other ways to detect optical spectra include using gratings, prisms, tunable filters, mock interferometers, Sagnac or common-path interferometers, and other means known to those of skill in the art. Many of these spectrometers also enable the spectrometer and detector to be treated as two distinct units with the spectral-separation occurring prior to the tissue. For example, an FTIR tunable filter, and a mock interferometer could all be placed prior to the tissue and impress an encoding on the light, which will subsequently be seen by the detector placed after the tissue as shown in FIG. 1.

In practicing the present invention, the tissue spectral data is determined by measuring the light intensity received by the output sensor at the various wavelengths which give indications of the absorption at such wavelengths of the infrared energy as a function of the composition of the tissue sample. As is well known in the art, a spectrum analyzer 30 of the present invention is able to convert the intensity of the infrared energy incident on the detector into a proportional amplitude of voltage. In this way, an output spectrum is defined for the tissue under analysis.

Once accurate and repeatable spectral data for tissue analysis is acquired, the second key element of the present invention is to define a methodology for training the device or instrument to identify spectral features or combinations of features that are unique for that particular individual and then to compare the database's spectral data and its unique features to new spectral data from supposedly the same individual to determine whether or not the spectral data in fact came from the same individual.

In a preferred method as depicted in FIGS. 8 and 9, the identification or verification task is implemented when a person seeks to perform an operation for which there are a limited number of people authorized (e.g., perform a spectroscopic measurement, gain entry into a room, achieve control over an interlocked vehicle or piece of machinery, pass through an immigration checkpoint, etc.). The person's spectral data is used for identification or verification of the person's identity. In this preferred method, the person initially enrolls in the system by collecting one or more representative tissue spectra in a database 800, 910 of a computer 900. If two or more spectra are collected during the enrollment, then these spectra be checked for consistency and recorded only if they are sufficiently similar, limiting the possibility of a sample artifact corrupting the enrollment data. For a verification implementation, an identifier 930 such as a PIN code, magnetic card number, username, badge, voice pattern, other biometric, or some other identifier would also be collected and associated with the confirmed enrollment spectrum or spectra.

In subsequent use, biometric identification would take place by collecting a spectrum 810, 920 from a person attempting to gain authorization. This spectrum would then be compared to the spectra in the enrolled authorization database 800, 910 and an identification made 830 if the match to an authorized database entry was better than a predetermined threshold. The verification task is similar, but would require that the person present the identifier in addition to a collected spectrum. The identifier would then be used to select a particular enrollment database spectrum and authorization would be granted if the current spectrum were sufficiently similar to the selected enrollment spectrum. If the biometric task is associated with an operation for which only a single person is authorized, then the verification task and identification task are the same and both simplify to an assurance that the sole authorized individual is attempting the operation without the need for a separate identifier.

Preferred implementations of the proposed verification methodology generate a difference spectrum, D(v), using the spectrum just collected from the person wishing authorization, V(v), and the enrolled authorized spectrum, A(v), or spectra corresponding to the person whose identification was stated:

$$D(v) = V(v) - A(v), \qquad \text{Eq. (1)}$$

where v is a variable designating the spectral frequency or wavelength, and D, V, A are spectral values in absorbance units or some related quantities. Alternatively, D, V, and A could be spectral intensity values, and the "difference" operation becomes an element-by-element ratio:

$$D(v) = V(v)/A(v) \qquad \text{Eq. (2)}$$

Other mathematical operations of a similar nature would also be possible to use for this application. For identification, a procedure similar to the verification case is followed, but it is repeated for each entry in the enrollment database.

The other key element of a preferred biometric method is a spectral calibration dataset that was developed using the same mathematical operation as used for generating D(v). The spectral differences (or ratio, etc.) in the calibration database are preferably formed from one or more people measured multiple times each. For robustness, the sampling of people included in the calibration database should span expected changes in the physiology, expected changes in or across the spectroscopic measurement devices, and changes in the measurement environment. In one preferred embodiment, spectral differences can be generated in a multitude of combinations of spectra from a given person, but should never be formed using spectra from different people. By filling the calibration database with intra-person difference spectra, typical inter-person spectral differences are removed, and the resulting calibration database contains only intra-person spectral features as well as instrumental and environmental effects.

The verification task is accomplished through determining if the spectral difference, D(v), is consistent with the calibration database. If the identification that the person stated is accurate, the resulting difference spectrum, D(v), will contain only intra-person spectral features, and thus, be consistent with the calibration database. Conversely, if the identification is not accurate, D(v) will contain inter-person spectral features and be incompatible with the intra-person spectral difference database for the individual. In this case, the verification will fail.

Similarly, identification is performed by comparing each of the difference spectra (one for each entry in the enrollment database) to the calibration database. Whichever difference(s) produces results that are consistent with the intra-person changes in the calibration database is (are) said to be the estimate of identity. If none of the differences produce results that are consistent with the calibration database, then the person attempting access is deemed to be an unauthorized intruder.

Consistency with the database can be ascertained in a variety of ways including linear discriminant analysis, quadratic discriminant analysis, K-nearest neighbors, neural networks, and other classification techniques. In preferred methods discriminant analysis techniques based upon multivariate analysis techniques are used. These methods rely upon establishing the underlying spectral shapes (factors, loading vectors, eigenvectors, latent variables, etc.) in the intra-person calibration database, and then using standard outlier methodologies (spectral F ratios, Mahalanobis distances, Eucliden distances, etc.) to determine the consistency of D(v) with the database. The underlying spectral shapes can be generated by multiple means as disclosed herein. First, the underlying spectral shapes can be generated based upon simple spectral decompositions (eigen analysis, Fourier analysis, etc.) of the calibration data.

The second method of generating underlying spectral shapes relates to the development of a generic model as described in U.S. Pat. No. 6,157,041, entitled "Methods and Apparatus for Tailoring Spectroscopic Calibration Models," the disclosure of which is incorporated by reference. In this application, the underlying spectral shapes are generated through a calibration procedure performed on intra-person spectral features.

In the third method the underlying spectral shapes can be generated by the development of a calibration based upon simulated constituent variation. The simulated constituent variation can model the variation introduced by real physiological or environmental or instrumental variation or can be simply be an artificial spectroscopic variation.

It is recognized that other means of classifying whether the spectral difference D(v), is or is not consistent with the database would be applicable to the identification and verification methods of the present invention. These methods could be used either in conjunction with, or in lieu of the aforementioned techniques.

Many variations in the methodology are possible within the scope of the present invention. In one embodiment, the entire spectrum is stored at substantially even wavelength or wavenumber intervals. In another embodiment, only preselected wavelengths of likely interest are recorded. In yet another embodiment, the spectral data are analyzed and stored as parameters capable of substantially regenerating the various spectra. In this latter embodiment, measurements at specific wavelengths outside of the parameters are not stored. The enrollment spectra can be stored in a database. In one embodiment, a number of enrollment spectra are obtained at one sitting and used to populate the verified spectra database. In another embodiment, spectra are obtained over several sittings for an individual.

As previously stated, spectral differences or distances can be obtained by performing calculations on different measurements taken at the same wavelength for the same individual. Variations in defining the spectral difference are possible. For the purpose of illustrating the invention consider first the case of measurement samples taken at a single wavelength. The spectral difference can take the form of a statistical analysis of the sample population, such as a mean measurement value and the standard deviation about the mean relative to a new spectral value at that wavelength. Various wavelengths can be evaluated in an attempt to maximize or minimize the standard deviation for the sample population. It may be desirable to select a wavelength to minimize the variation for that wavelength for samples taken for a single individual while maximizing inter-person variation, to allow for distinguishing or discriminating between the authorized person and an impostor. For example, a wavelength that did not vary between people would not be useful for biometric discrimination. At the same time, it is desirable to select a wavelength that does not also vary a great deal between measurements for the same individual, as the intra-person differences can swamp the inter-person differences.

In the simple, single wavelength case discussed above, a wavelength could be selected that maximized inter-person spectral differences while minimizing intra-person spectral differences. In this one-dimensional example, a wavelength could be selected that tended to cluster the measurements for each individual tightly about a single point along an axis, while spreading these tight clusters along the axis for the numerous individuals. When a target sample is introduced, the measurement taken can be compared with the cluster of values for the individual for that purported identity. A threshold can be established for each cluster of values for a verified individual. For example, a threshold could be set at two standard deviations for the sample population, with any measurements falling outside of this range being rejected, and the target individual verification refused.

From the above simplified single wavelength example, the theory of analyzing the spectral data can be expanded. In a two-wavelength example, two wavelengths could be selected and the two wavelength measurements plotted against each other as X-Y coordinates in a two-dimensional plot. The X-Y plot would preferably show a series of clusters, each corresponding to different individuals measured multiple times, widely separated from each other. The spread of these clusters could be used to assess normal within person variation, and could be used to establish a probability value about the mean position of each cluster, such that a certain percentage of all measurements on a given person are expected to fall within a certain region around the mean cluster position.

When enrollment data are taken in the two-wavelength case, the position of each enrolled person can be plotted on a similar X-Y plot. A region around each enrollment point can be drawn using the information generated in the calibration set to establish a probability boundary such that a high fraction, such as 99%, of all subsequent measurements collected on each enrolled person are expected to fall within this region. For subsequent spectral biometric identification, data are collected and plotted on this same X-Y graph. If the collected data falls within one of the 99% probability regions then the person can be said to be identified as the appropriate enrolled individual. If the test data point does not lie within any of the 99% probability boundaries then the person under test is likely to not be enrolled or authorized and should retake the measurement in case there was an error in the first measurement. If the clustering of the enrolled data is such that the test data falls within two or more probability regions, then the authorization is confirmed but the identification is ambiguous. If the absolute identification is important to the task, such as for establishing personality settings in an automobile, then a probability can be calculated for each of the candidate identities and the one with greatest probability is used. Finally, if the biometric task is a verification request rather than identification, then the preceding method is followed using just the single candidate enrollment data point.

Similarly, a three-wavelength example of the application of this analysis can be envisioned, represented by clusters of data points being plotted in three-dimensional space, and the geometric distance of a target point from a cluster being determined. By extension, ten wavelengths could be selected and the distance of a target point from a cluster calculated in ten-dimensional space. While not as easily envisioned, multiple wavelengths are used in preferred embodiments.

In an alternative method, functions are used to preprocess spectral measurement values and the resulting function value used rather than the direct measurement. For example, measurement values taken at two wavelengths may be observed to vary up and down, opposite from one another, for an individual, but the average or total of these two values may be seen to be remain constant for that individual. In this example, a plot of the two measurements against each other from several sittings could show a cluster about a line segment having negative slope. A one-dimensional plot of the total or average would show a tight cluster about a single point. In this way, multiple wavelengths may be preprocessed with functions to result in a single value, and the single value used in place of the direct measurements. In a preferred embodiment, functions (also known as factors, loading vectors, eigenvectors, latent variables, classification features), which represent weighted combinations of the raw measurements at each wavelength, are generated using techniques such as Principal Component Analysis, Singular Value Decomposition, Linear Discriminant Analysis, or other methods as are known to one of skill in the art. The advantages of decomposing the data into a set of factors include the increased accuracy, speed and stability of the resulting analysis, as well as a dimension reduction that may facilitate human visualization. Once the decomposition of the raw data is performed the resulting magnitudes of the factors can be used in a manner identical to the multi-wavelength examples provided above.

Selection of which wavelengths to use can be important. One method of selecting wavelengths is discussed in U.S. Pat. No. 5,435,309. In one method, wavelengths of interest are selected a priori and used for all samples. In another method, the measurements are periodically used to recalculate inter-person and intra-person differences. The addition of new otherwise closely clustered or even overlapping, individuals into an authorization database can be remedied by choosing different wavelengths, or different functions operating upon these wavelengths.

In use, tissue spectral data can be taken from forearm undersides of individuals, any of the phalanges on the dorsal or ventral surfaces of the fingers and thumbs, the dorsal or ventral sides of the wrist, the thenar eminence, the hypothenar eminence, the medial hypothenar eminence, or other sites convenient and suitable sites, as previously described. The tissue spectral data can then be stored in a computer database. In general, either before or after storage, the magnitude of the underlying spectral shapes and properties such as factors and their magnitudes can be established. Standard outlier methodologies such as spectral F ratios, Mahalanobis distances, and Euclidean distances can be used to determine the consistency of the target spectrum with the spectral authorization database for the person with the purported identity.

In one method, after a sufficient number of calibration spectra have been collected, the calibration database is operated upon by software and discriminant analysis performed on the data, generating the appropriate factors. In one method, Principle Component Analysis is applied to the calibration data to generate factors. In another method, discriminant analysis is performed to generate factors useful in clustering the intra-person data points together, while separating the clusters at a large inter-person distance. Examples of discriminant analysis methods useful in conjunction with the present invention include linear discriminant analysis and quadratic discriminant analysis, and other non-linear discriminant analysis techniques.

In one method when identity verification 1100 is desired as shown in FIGS. 10 and 11, a tissue spectrum 1000, 1110 and purported identity 1010, 1120 are obtained from the target individual. The current tissue spectrum is subtracted from the appropriate enrollment spectrum, producing a spectral difference 1020. The spectral difference 1020 can then be decomposed using the factors generated from the calibration dataset and the consistency between the spectral difference and the calibration set can be calculated 1140. One calculation measures the Mahalanobis distance of the spectral difference with respect to the calibration factor set. If the distance is less than a threshold distance, then the purported identity can be positively verified 1030, 1130. Another calculation generates the spectral residuals of the spectral difference with respect to the calibration factor set. If the residuals are less than a predetermined threshold value, then the purported identity can be positively identified 1150. In another method, both the spectral residual and the Mahalanobis distance must be below their respective thresholds before identity is positively established.

Experimental Results

An experiment was conducted to determine the viability of utilizing the methodology disclosed herein to verify the identification of an individual. The instrumentation utilized was a near infrared Fourier transfer spectrophotometer manufactured by Perkin Elmer. The specific model used as a Perkin Elmer 2000. The sampling of the human tissue was done on the volar side of the forearm. The optical sampling device was a fiber optic sampling device that had separate fibers for launching light into the tissue and fibers for collecting the light exiting the tissue. An index matching fluid was placed between the arm and the fiber optic sampling head. The resulting intensity spectra were converted into absorbance spectra and scaled by a vector wavelength. Spectra were recorded and subsequently processed in the wavelength range of 4,200 to 7,200 $cm^{-1}$. The data consisted of sitting average spectra (5 samples per sitting) measured for 288 different people. Each were measured for a single sitting sometime within a 5-week time span. As well, there were three people measured for multiple sittings over the same 5-week span (nominally 10 times).

The framework for the investigation assumed a calibration model, a spectral database consisting of spectra from a large number of individuals against whom matching was performed, and a spectrum from an unknown individual (target spectrum). The verification task was to properly identify the target spectrum as either the specified person or to determine that the person did not properly identify himself.

The discrimination method applied in this case relied on Mahalanobis distance and the spectral residual magnitude that were generated when a difference spectrum was presented to the calibration model. The spectral difference was formed between the target spectrum and a test spectrum in the database. If the value of the Mahalanobis distance and the spectral residual for a given spectral difference pair were both below a prescribed level, the two spectra were determined to have come from the same individual. If one or both metrics were greater than their respective thresholds, the determination was made that the two spectra came from different individuals.

Thresholds for the two metrics were set by examining the respective cumulative distribution functions for the full-model calibration data. Two threshold values were used for this investigation: one pair that each encompassed 99% of the calibration data ("lenient") and one pair such that each encompassed only 95% of the calibration data ("stringent").

The false positive error rate was examined by using the 288 individual people's spectra in a round-robin fashion. Each was pulled out of the database and an evaluation made of how many of the remaining people in the database matched this spectrum at each of the two similarity thresholds. The false negative error rate was examined by looking at the degree of matching observed between sittings of the same person (performed for each of the three repeat people).

When the threshold values were set to the more lenient threshold (99%), the round-robin results showed the number of "matches" that occurred when each of the 288 people is pulled out from the spectral library and evaluated relative to the remaining 287 people's spectra. On average, each person matched 0.5 of another person within this database, yielding a false positive rate of 0.17%. This is the error rate that occurs when a person not in the database incorrectly specifies that he is one of the library people and the measurement confirms this.

In a subsequent test, one of the people, who was measured repeatedly over the 5-week data collection period, was compared to all other observation using the same verification methodology described above. Using the lenient threshold, every sitting matches with every other sitting, resulting in a false negative error rate of 0.0%. Results from the other two repeat people were similar.

When the verification threshold was set to the slightly more stringent standard (95%), the cross-person and same person results showed there were no matches observed across people, resulting in a false positive error rate of 0.0%. The same person, cross-sitting results show a diminished ability to match any one sitting with any other one sitting, leading to a single-sample false negative error rate of greater than 30%. However, if the spectral library consists of multiple samplings of the person in different physiologic states, the verification results can be greatly improved. In this case, if the spectral library consists of all nine of the remaining samples, then 100% of the time one or more (actually 3 or more) of the spectral library entries match the target spectrum, resulting in a false negative error rate of 0.0%. Results from the other two repeat people were similar.

The present invention has been disclosed with focus on in-vivo analysis on people. It is, however, recognized that the present methods and techniques can be used for in-vivo analysis of other biological organisms such as cows, horses, and other livestock to identify or confirm identity of the animal. As well the present methods and techniques can also be applied to in-vitro analysis of blood, tissue or fluid samples to identify or confirm identity of a sample.

The biometric capabilities in the 1.1–2.5 $\mu$m NIR spectral region were also examined using a laboratory system to collect optical samples on a group of volunteer subjects. The system consisted of a 40 W quartz tungsten halogen source, a fiber optic sampler assembly, a Bomem WorkIR spectrometer operating with a spectral resolution of 16 cm$^{-1}$ and a 1 mm$^2$ InGaAs detector. The optical sampler consisted of six different illumination-detection bundles that had a source-detector spacing of approximately 0.6 mm. In this case, no index matching fluid was used between the sampler and the tissue. The data were collected from 87 diabetic subjects who participated in a portion of a 17-week study. Approximately half of the subjects participated in the study for 6 weeks and half participated for 11 weeks. In either case, each person was measured during two separate visits per week for each week they participated in the study. During each measurement visit, multiple (3–5) optical samples were collected from the underside of their left forearm. Each optical sample consisted of 90 seconds of measurement time. A total of more than 5100 optical samples were collected on this study group. The resulting intensity spectra were log-transformed to pseudo-absorbance data and a scale function was applied to the spectra to make the spectral noise characteristics uniform. Standard outlier metrics (Mahalanobis Distance and Spectral F-Ratio) were applied to the resulting scaled absorbance data to remove outlying spectra before subsequent processing.

The biometric analysis was performed by randomly selecting 30 subjects' data as from authorized users ("validation"), selecting 10 that were from non-authorized users ("intruders"), and the remaining subjects' data were used to build a calibration set. The calibration data were processed to produce generic data as described in U.S. Pat. No. 6,157,041, entitled "Methods and Apparatus for Tailoring Spectroscopic Calibration Models". A PCA decomposition of these data was performed to generate 50 eigenvectors and scores. The scores were then analyzed to determine the 20 factors that had the largest values for the ratio of the between-person variation to the within-person variation for each set of scores.

The first two samples for each of the validation subject's data were averaged and used as 30 initial enrollment spectra. Each of the remaining validation spectra were taken in temporal sequence and subtracted from the enrollment spectrum. This spectral difference was then presented to the selected calibration factors and a Mahalanobis distance was calculated. If the Mahalanobis distance was below a certain threshold value, the validation spectrum was deemed valid, and a weighted sum of the validation spectrum (0.2) and the enrollment spectrum (0.8) was used to update the enrollment spectrum. This process was repeated for multiple threshold values. One of ordinary skill in the art will recognize that the Spectral F-Ratio could be used instead of or in conjunction with the Mahalanobis distance metric to perform the identity determinations.

Figure 4:
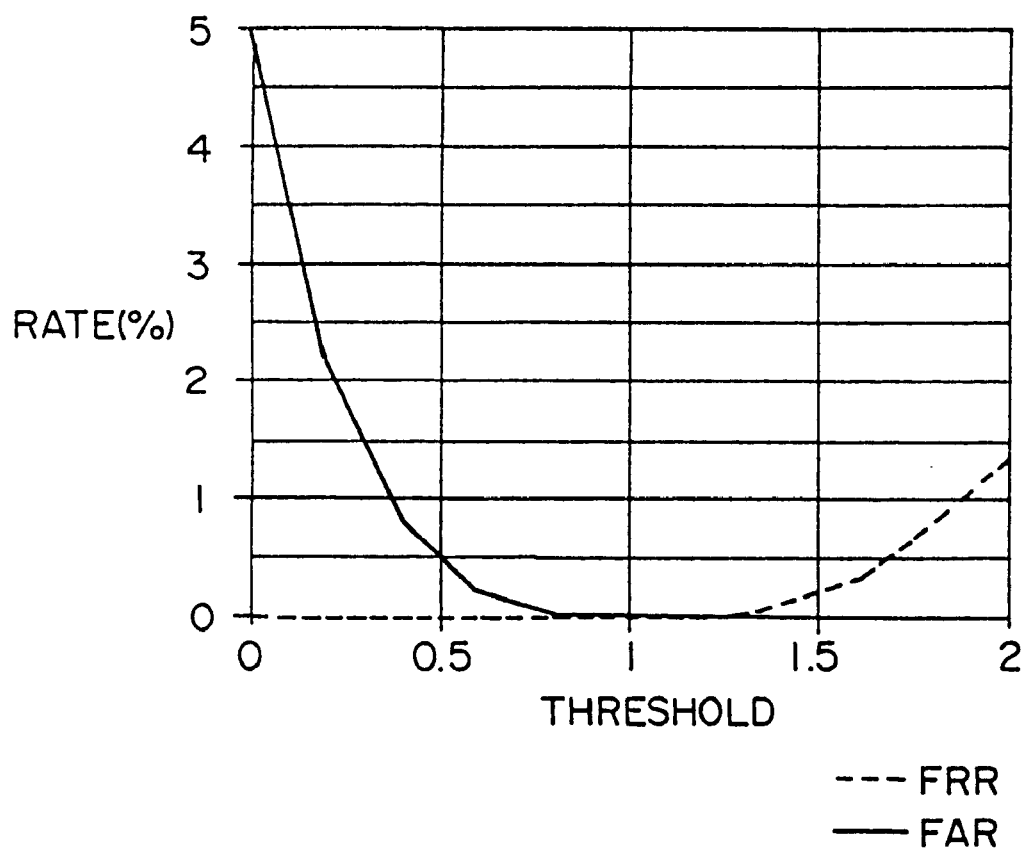
FIG. 4 is a graph depicting false acceptance rates and false rejection rates for a near-infrared biometric apparatus of the present invention.
Figure 5:
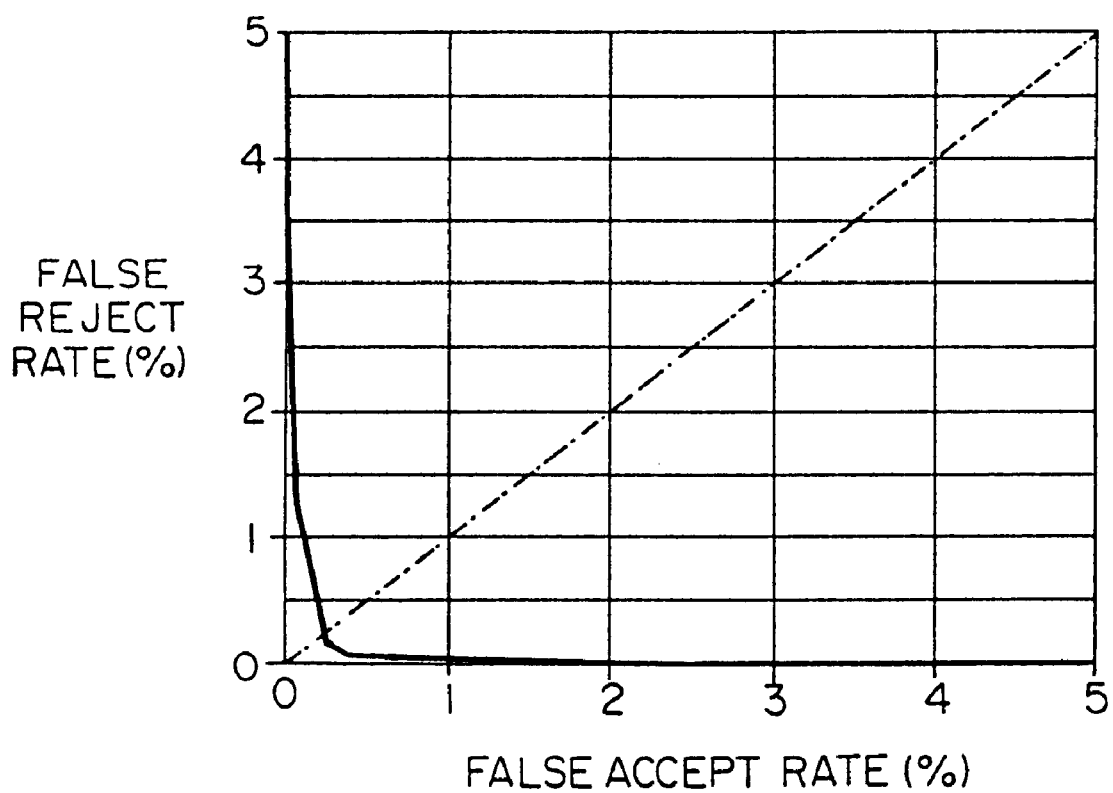
FIG. 5 is a graph summarizing receiver operating characteristics for the biometric analyzer of FIG. 4.

The intruder data was processed in a similar manner as the validation data using the same threshold values. The resulting performance plots are shown in FIGS. 4 and 5. FIG. 4 shows the false acceptance rate (FAR) and the false rejection rate (FRR) as a function of the threshold value. FIG. 5 shows the corresponding receiver operating characteristics (ROC) curve for these data. The Equal Error Rate (EER: FAR= FRR) for these data is approximately 0.2% demonstrating a high degree of biometric capability over an extended period of time.

Subsequently, the same NIR system described above was used to perform identification tasks using multiple tissue sites on numerous non-diabetic volunteers. Tissue sites that were tested and established to for spectral identification and verification included the dorsal and ventral surfaces of the forearm, any of the phalanges on the dorsal or ventral surfaces of the fingers and thumbs, the dorsal or ventral sides of the wrist, the thenar eminence, the hypothenar eminence, the medial hypothenar eminence, the web between the index finger and the thumb, and the forehead. The use of a particular site required a methodology similar to that described above. Each new site required that the calibration data include data collected at that tissue site. Once the proper calibration data were collected and processed to generate factors, the site could then be used for subsequent enrollment and testing. In all cases, sites that had contralateral or multiple counterparts could be used nearly interchangeably: a person could enroll with the left index finger and use the right index finger (or any other finger) to perform the biometric task.

Figure 6:
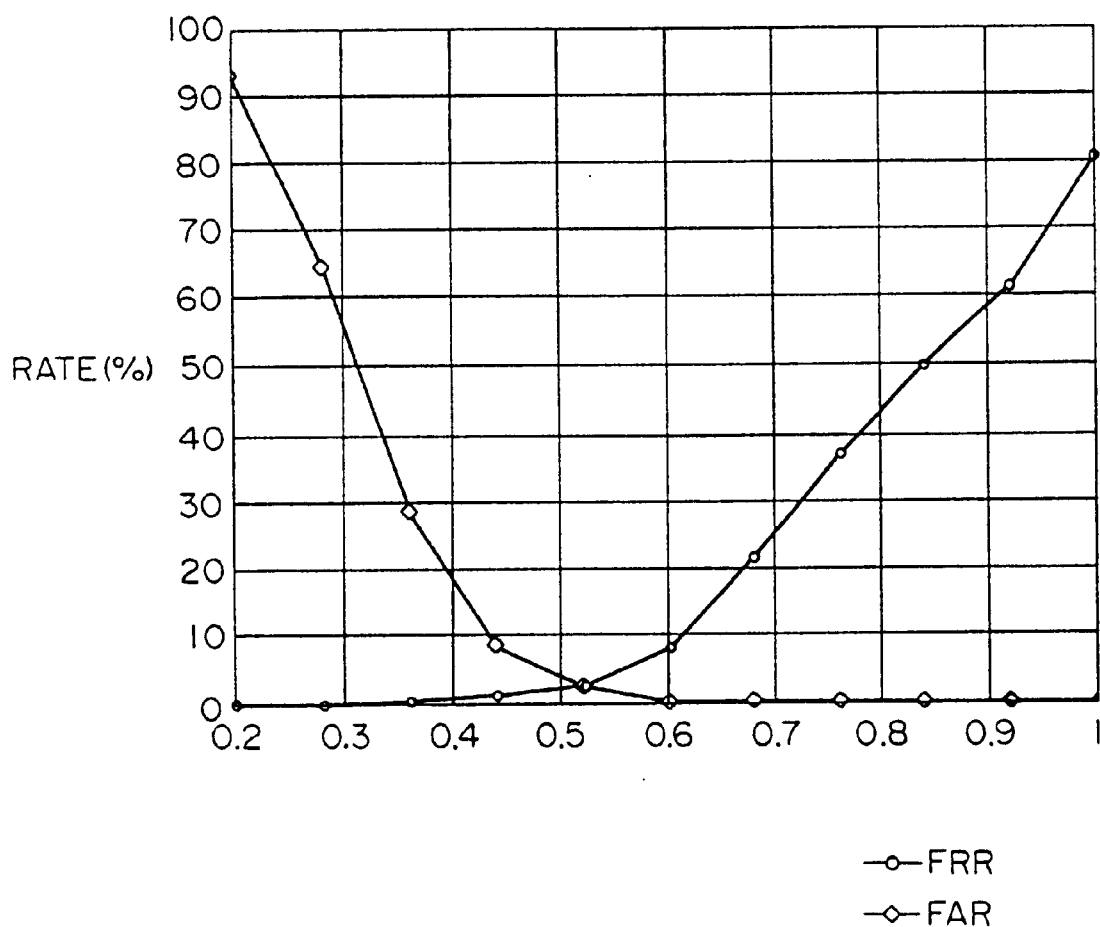
FIG. 6 is a graph depicting false acceptance rates and false rejection rates for a biometric sensor of the present invention operating in the near-ultraviolet, visible, and very near infrared region of the spectrum.
Figure 7:
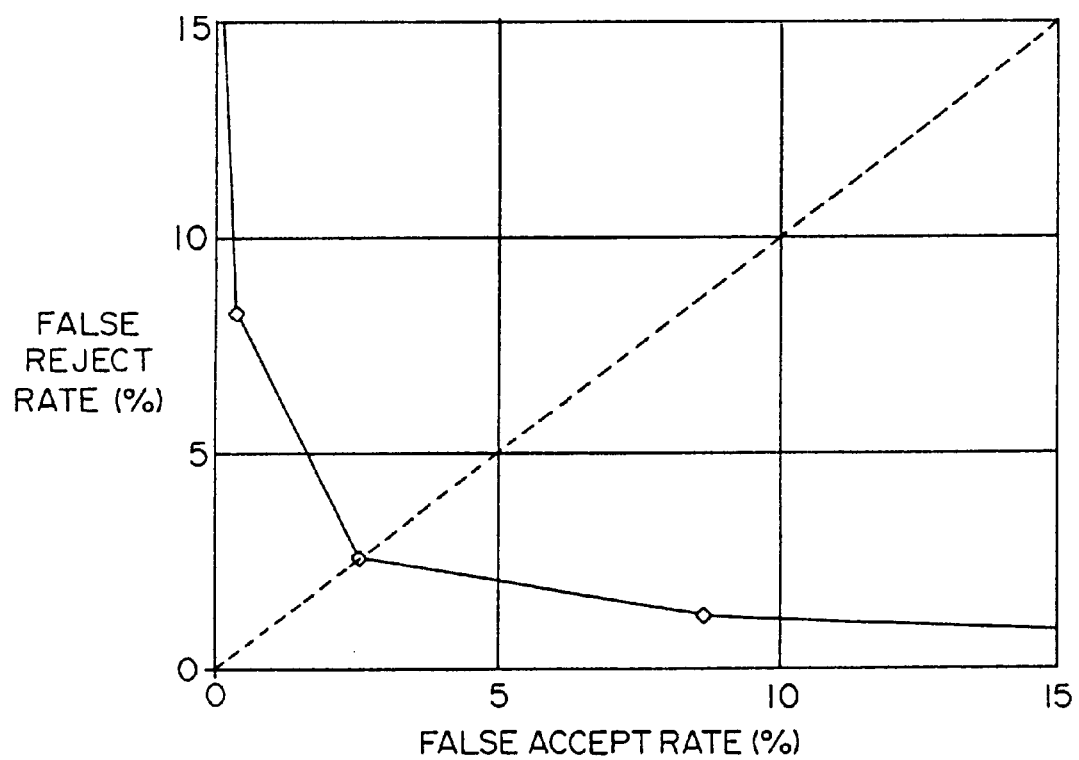
FIG. 7 is a graph depicting receiver operating conditions for the biometric sensor of FIG. 6.

The same 87 subjects that were used to collect the near infrared data described above were also simultaneously sampled with a silicon-region system. An Ocean Optics grating array spectrometer with a 1×2048 silicon linear CCD array and 12-bit digitization was used in conjunction with a fiber optical probe to collect spectral data that spanned the spectral range from 350 nm to 1000 nm. The spectral data were collapsed using an 8-point moving-window averaging filter to produce 256 data points per spectrum. These data were processed and analyzed in a manner similar to the NIR data, producing the results shown in FIG. 6 (FAR and FRR) and FIG. 7 (ROC), with an equal error rate of 2.6%. While the results are not quite as good as produced by the NIR system, they strongly indicate that biometric determinations can be made in the silicon-region. Analysis of the silicon and near infrared data showed that the silicon data contained significantly greater noise due to instrumental variation, which was likely due to a sub-optimal setup of this system and had an adverse impact on the measured results.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. A system for verifying the purported identity of a target individual comprising:

an enrollment database including sub-epidermal tissue optical spectra collected from at least one enrolled person, said enrolled person's sub-epidermal tissue optical spectra having a plurality of measurement wavelengths obtained by applying a spectral band of optical wavelengths to said sub-epidermal tissue;

means for obtaining at least one sub-epidermal tissue optical spectra and purported identity from said target individual, said target individual's sub-epidermal tissue optical spectra having a plurality of measurement wavelengths obtained by applying said spectral band of optical wavelengths to sub-epidermal tissue of said target individual;

means for comparing said target individual sub-epidermal tissue optical spectra and said enrolled person's sub-epidermal tissue optical spectra by selecting for comparison a combination of individual wavelengths of said band emanating from said sub-epidermal tissue that are unique to said person and insensitive to environmental and instrumental effects, said enrolled person's sub-epidermal tissue optical spectra corresponding to the purported identity of the target individual, said comparison providing a measure of the degree of similarity between said target individual sub-epidermal tissue optical spectra and said enrolled person's sub-epidermal tissue optical spectra; and means for positively verifying said target individual's identity by confirming that said target individual's measure of spectral similarity is at least as similar as an established threshold value.

2. The system as recited in claim 1, wherein said means for obtaining said target individual sub-epidermal tissue optical spectra includes a spectrometer.

3. The system as recited in claim 2, wherein said spectrometer is an FTIR spectrometer.

4. The system as recited in claim 2, wherein said spectrometer is a grating array spectrometer.

5. The system as recited in claim 1, wherein said optical spectra include near-infrared wavelengths.

6. The system as recited in claim 1, wherein said optical spectra include visible wavelengths.

7. The system as recited in claim 1, wherein said optical spectra include near-ultraviolet wavelengths.

8. The system as recited in claim 1, wherein said comparison and similarity determination utilizes a classification algorithm.

9. A system for identifying a target individual comprising:

an enrollment database including sub-epidermal tissue optical spectral data collected from one or more enrolled persons, said enrolled persons' sub-epidermal tissue optical spectra having a plurality of measurement wavelengths obtained by applying a spectral band of optical wavelengths to said sub-epidermal tissue;

means for obtaining at least one sub-epidermal tissue optical spectra from said target individual, wherein said means for obtaining said target individual sub-epidermal tissue optical spectra includes means for measuring optical radiation reflected from sub-epidermal tissue of said target individual, said target individual's sub-epidermal tissue optical spectra having a plurality of measurement wavelengths obtained by applying said spectral band of optical wavelengths to sub-epidermal tissue of said target individual;

means for comparing said target individual sub-epidermal tissue optical spectra and said all enrolled persons' sub-epidermal tissue optical spectra by selecting for comparison a combination of individual wavelengths of said band emanating from said sub-epidermal tissue that are unique to each said person and insensitive to environmental and instrumental effects, said comparison providing a measure of the degree of similarity between said target individual's sub-epidermal tissue optical spectra and each said enrolled person's sub-epidermal tissue optical spectra; and means for indicating identity as at least one of the said enrolled persons if the corresponding measure of degree of similarity is at least as similar as an established threshold value.

10. The system as recited in claim 9, wherein said means for obtaining said target individual's sub-epidermal tissue optical spectra includes a spectrometer.

11. The system as recited in claim 10, wherein said spectrometer is an FTIR spectrometer.

12. The system as recited in claim 10, wherein said spectrometer is a grating array spectrometer.

13. The system as recited in claim 9, wherein said optical spectra include near-infrared wavelengths.

14. The system as recited in claim 9, wherein said optical spectra include visible wavelengths.

15. The system as recited in claim 9, wherein said optical spectra include near-ultraviolet wavelengths.

16. The system as recited in claim 9, wherein said comparison and similarity determination utilizes a classification algorithm.

17. A system for verifying the purported identity of a target individual comprising:

a computer including an input device and an output device;

an enrollment database including sub-epidermal tissue optical spectra for at least one enrolled person, said enrolled person's sub-epidermal tissue optical spectra having a plurality of measurement wavelengths obtained by applying a band of optical wavelengths to said sub-epidermal tissue;

means for obtaining at least one sub-epidermal tissue optical spectrum from said target individual, including an optical radiation source, an optical sampler for projecting optical radiation into the sub-epidermal tissue and for collecting radiation that substantially passed through sub-epidermal sub-epidermal tissue, an optical spectrometer for measuring the sub-epidermal optical intensity over a plurality of wavelengths, wherein said target individual's sub-epidermal tissue optical spectrum has a plurality of measurement wavelengths obtained by applying said spectral band of optical wavelengths to sub-epidermal tissue of said target individual;

means for obtaining said target individual's purported identity; and a program running in said computer for comparing said target individual sub-epidermal tissue optical spectrum and said enrolled person's sub-epidermal tissue optical spectra corresponding to said target individual's purported identity by selecting for comparison a combination of individual wavelengths of said band emanating from said sub-epidermal tissue that are unique to said person and insensitive to environmental and instrumental effects.

18. A system for identifying a target individual comprising:

a computer including an input device and an output device;

an enrollment database including sub-epidermal tissue optical spectra for at least one enrolled person, said enrolled persons' sub-epidermal tissue optical spectra having a plurality of measurement wavelengths obtained by applying a spectral band of optical wavelengths to said sub-epidermal tissue;

means for obtaining at least one sub-epidermal tissue optical spectrum from said target individual, including an optical radiation source, an optical sampler for projecting optical radiation into the sub-epidermal tissue and for collecting radiation that substantially passed through sub-epidermal sub-epidermal tissue, an optical spectrometer for measuring the sub-epidermal optical intensity over a plurality of wavelengths, wherein said target individual's sub-epidermal tissue optical spectrum has a plurality of measurement wavelengths obtained by applying said spectral band of optical wavelengths to sub-epidermal tissue of said target individual; and a program running in said computer for comparing said target individual sub-epidermal tissue optical spectrum and all said enrolled persons' sub-epidermal tissue optical spectra by selecting for comparison a combination of individual wavelengths of said band emanating from said sub-epidermal tissue that are unique to each said person and insensitive to environmental and instrumental effects.

19. A method for verifying the purported identity of a target individual utilizing an enrollment database including sub-epidermal tissue optical spectra collected from a number of enrolled individuals having known identities, said sub-epidermal tissue optical spectra having a plurality of measurement wavelengths obtained by applying a spectral band of optical wavelengths to said sub-epidermal tissue, comprising the steps of:

obtaining optical target sub-epidermal tissue spectral data from said target individual, said optical target sub-epidermal tissue spectral data having a number of measurement wavelengths obtained by applying said spectral band of optical wavelengths to sub-epidermal tissue of said target individual;

obtaining said purported identity from said target individual;

comparing said optical target sub-epidermal tissue spectra and an enrolled individual's sub-epidermal tissue optical spectra by selecting for comparison a combination of individual wavelengths of said band emanating from said sub-epidermal tissue that are unique to said enrolled individual and insensitive to environmental and instrumental effects, said enrolled individual's sub-epidermal tissue optical spectra corresponding to the purported identity of the target individual, said comparison providing a measure of the degree of similarity between said optical target sub-epidermal tissue spectra and said enrolled individual's sub-epidermal tissue optical spectra; and positively verifying said target individual's identity by confirming that said target individual's measure of spectral similarity is at least as similar as an established threshold value.

20. The method for verifying the identity of a target individual as recited in claim 19, wherein the method further includes a classification algorithm to perform said comparison between said target individual's optical spectral data and said enrolled individual's optical spectral data.

21. The method for verifying the identity of a target individual as recited in claim 20, wherein the method further includes classification features that are determined from a set of calibration optical spectral data collected on at least one individual measured more than one time.

22. The method for verifying the identity of a target individual as recited in claim 21, wherein said classification features are applied to the said comparison between the target optical spectral data and the enrollment spectral data to determine the similarity with respect to the said classification features.

23. The method for verifying the identity of a target individual as recited in claim 22, wherein said verification occurs when said comparison of said target optical spectral data and said enrollment spectral data using said classification features is at least as good a predetermined measure of similarity.

24. The method for identifying a target individual as recited in claim 19, further comprising an enrollment database with optical spectral data collected from a number of enrolled individuals, wherein said number is greater than one.

25. The method for identifying a target individual as recited in claim 19, further comprising an enrollment database with optical spectral data collected from a number of enrolled individuals, wherein said number is equal to one.

26. The method for identifying a target individual as recited in claim 19, wherein said target spectrum is added to said enrollment optical spectral data after said verification of identity.

27. The method for identifying a target individual as recited in claim 19, wherein said sub-epidermal tissue optical spectra include near-ultraviolet wavelengths.

28. The method for identifying a target individual as recited in claim 19, wherein said sub-epidermal tissue optical spectra include visible wavelengths.

29. The method for identifying a target individual as recited in claim 19, wherein said sub-epidermal tissue optical spectra include near-infrared wavelengths.

30. A method for identifying a target individual utilizing an enrollment database including sub-epidermal tissue optical spectra collected from a number of enrolled persons, said sub-epidermal tissue optical spectra having a plurality of measurement wavelengths obtained by applying a spectral band of optical wavelengths to said sub-epidermal tissue, comprising the steps of:

obtaining optical target sub-epidermal tissue spectral data from said target individual, said optical target sub-epidermal tissue spectral data having a number of measurement wavelengths and including a substantial spectral contribution from sub-epidermal tissue, wherein said measurement wavelengths are obtained by applying said spectral band of optical wavelengths to sub-epidermal tissue of said target individual;

comparing said optical target sub-epidermal tissue spectral data and said enrolled persons' sub-epidermal tissue optical spectra by selecting for comparison a combination of individual wavelengths of said band emanating from said sub-epidermal tissue that are unique to each said person and insensitive to environmental and instrumental effects, said comparison providing a measure of the degree of similarity between said optical target sub-epidermal tissue spectral data and each of said enrolled person's sub-epidermal tissue optical spectra; and positively establishing said target individual's identity by confirming that said target individual's measure of spectral similarity is at least as similar to one of the enrolled person's optical spectral data as an established threshold value.

31. The method for identifying a target individual as recited in claim 30, wherein the method further includes a classification algorithm to perform said comparison between said target individual's optical spectral data and said enrolled persons' optical spectral data.

32. The method for identifying a target individual as recited in claim 31, wherein the method further includes classification features that are determined from a set of calibration optical spectral data collected on at least one individual measured more than one time.

33. The method for identifying a target individual as recited in claim 32, wherein said classification features are applied to the said comparison between the target optical spectral data and the enrollment spectral data to determine the similarity with respect to the said classification features.

34. The method for identifying a target individual as recited in claim 33, wherein said identification occurs when said comparison of said target optical spectral data and said enrollment spectral data using said classification features is at least as similar as a predetermined measure of similarity for a number of enrolled persons' optical spectral data.

35. The method for identifying a target individual as recited in claim 34, wherein the target identity is chosen as the most similar of all said enrolled persons whose enrollment spectral data are at least as similar to the said target spectral data as a predetermined measure of similarity.

36. The method for identifying a target individual as recited in claim 30, further comprising an enrollment database with optical spectral data collected from a number of enrolled persons, wherein said number is greater than one.

37. The method for identifying a target individual as recited in claim 30, further comprising an enrollment database with optical spectral data collected from a number of enrolled persons, wherein said number is equal to one.

38. The method for identifying a target individual as recited in claim 30, wherein said target spectrum is added to said enrollment optical spectral data after said identification.

39. The method for identifying a target individual as recited in claim 30, wherein said sub-epidermal tissue optical spectra include near-ultraviolet wavelengths.

40. The method for identifying a target individual as recited in claim 30, wherein said sub-epidermal tissue optical spectra include visible wavelengths.

41. The method for identifying a target individual as recited in claim 30, wherein said sub-epidermal tissue optical spectra include near-infrared wavelengths.

42. A system for identifying a target individual comprising:

an enrollment database including sub-epidermal tissue optical spectra collected from at least one enrolled person, each of said enrolled person's sub-epidermal tissue optical spectrum having a plurality of measurement wavelengths obtained by applying a spectral band of optical wavelengths to said sub-epidermal tissue;

a spectrometer adapted to obtain at least one sub-epidermal tissue optical spectrum from said target individual by measuring optical radiation reflected from sub-epidermal tissue of said target individual, said target individual's sub-epidermal tissue optical spectrum having a plurality of measurement wavelengths obtained by applying said spectral band of optical wavelengths to sub-epidermal tissue of said target individual;

a comparator adapted to compare said target individual sub-epidermal tissue optical spectrum and each said enrolled person's sub-epidermal tissue optical spectrum by selecting for comparison a combination of individual wavelengths of said band emanating from said sub-epidermal tissue that are unique to each said person and insensitive to environmental and instrumental effects and provide a measure of a degree of similarity between said target individual's sub-epidermal tissue optical spectrum and said enrolled person's sub-epidermal tissue optical spectrum; and an indicator adapted to identify at least one of said enrolled persons if the corresponding measure of the degree of similarity meets an established threshold value.

43. The system recited in claim 42, wherein said optical spectra include near-infrared wavelengths.

44. The system recited in claim 42, wherein said optical spectra include visible wavelengths.

45. The system recited in claim 42, wherein said optical spectra include near-ultraviolet wavelengths.

* * * * *